United States Patent [19]

Mehlhorn et al.

[11] Patent Number: 5,464,837
[45] Date of Patent: Nov. 7, 1995

[54] METHOD FOR CONTROLLING FISH PARASITES USING TRIAZINE DIONE DERIVATIVES

[75] Inventors: Heinz Mehlhorn, Neuss-Odesheim; Günter Schmahl, Bochum; Werner Lindner, Cologne; Axel Haberkorn, Wuppertal, all of Germany

[73] Assignee: Bayer Aktiengesellschaft, Leverkusen, Germany

[21] Appl. No.: 913,758

[22] Filed: Jul. 13, 1992

Related U.S. Application Data

[63] Continuation of Ser. No. 617,473, Nov. 26, 1990, abandoned, which is a continuation of Ser. No. 376,085, Jul. 6, 1989, abandoned.

[30] Foreign Application Priority Data

Jul. 30, 1988 [DE] Germany ............................ 38 26 058.1

[51] Int. Cl.⁶ .................................................... A61K 31/53
[52] U.S. Cl. .......................................... 514/242; 424/405
[58] Field of Search ................................................ 514/242

[56] References Cited

U.S. PATENT DOCUMENTS

| | | | |
|---|---|---|---|
| 4,207,354 | 6/1980 | Haga et al. | 426/574 |
| 4,284,653 | 8/1981 | Shigeoka et al. | 426/312 |
| 4,631,278 | 12/1986 | Boeckx et al. | 514/242 |
| 4,640,917 | 2/1987 | Rosner et al. | 514/242 |
| 4,933,341 | 6/1990 | Lindner et al. | 514/241 |
| 4,935,423 | 6/1990 | Lindner et al. | 514/242 |
| 4,968,795 | 11/1990 | Lindner et al. | 544/182 |
| 5,023,260 | 6/1991 | Lindner et al. | 514/269 |

FOREIGN PATENT DOCUMENTS

| | | |
|---|---|---|
| 0170316 | 5/1986 | European Pat. Off. |
| 8600072 | 3/1986 | WIPO |

OTHER PUBLICATIONS

Parasitology Research (1989) 75:503–511, "Chemotherapy of fish parasites", Günter Schmahl, Horst Taraschewski and Heinz Mehlhorn.

Lehrbuch der Parasitologie, Herausgegeben von Prof. Dr. Sc. Med. Vet. Theodor Hiepe vol. 2, Veterinarmedizinishce Protozoologie, Von Theodore Heipe und Ruth Jungmann.

*Primary Examiner*—Jyothsna Venkat
*Attorney, Agent, or Firm*—Sprung Horn Kramer & Woods

[57] ABSTRACT

A method for controlling fish parasites by administering to fish having such parasites or to a habitat of fish having such parasites an effective amount of at least one substituted 1,2,4-triazinedione of the formula

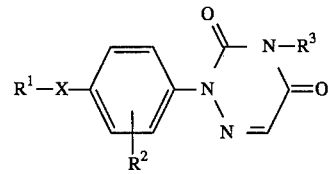

in which $R^1$ represents optionally substituted aromatic radicals or represents optionally substituted heteroaromatic radicals linked via carbon;

X represents O, S, SO, $SO_2$ or -CH(CN)-;

$R^2$ represents one or more identical or different hydrogen, halogen, nitro, alkyl, alkoxy, halogenoalkyl, or halogenoalkoxy radicals; and $R^3$ represents hydrogen, optionally substituted alkyl, alkenyl, alkinyl, or aralkyl;
or a salt thereof with a base.

8 Claims, No Drawings

METHOD FOR CONTROLLING FISH PARASITES USING TRIAZINE DIONE DERIVATIVES

This application is a continuation of Ser. No. 07/617,473, filed Nov. 26, 1990, now abandoned which is a continuation of Ser. No. 07/376,085, filed Jul. 6, 1989, now abandoned.

The present invention relates to agents containing 1,2,4-triazinediones, against fish parasites, in particular parasitic Protozoa (unicellular organisms) and Metazoa (multicellular organisms).

The Protozoa and Metazoa include classes which are common as fish parasites. In large-scale animal keeping in large fish farms they represent a serious problem since infestation can spread rapidly through the entire livestock. These parasites represent a large problem for rearing, in particular for young and sensitive fish, and they cause considerable losses.

Some parasitic Protozoa and Metazoa are attached to skin and gills of the fish and in this way cause skin injuries which render the fish susceptible to bacterial, viral or fungal infection. They are also vectors for viral infections. Some of the parasitic Protozoa and Metazoa also infest internal organs of the fish (for example intestines, bones) and cause growth deformations or the death of the fish.

Only a few agents for the control of the parasitic Protozoa and Metazoa are known. However, their action is not always completely satisfactory. Moreover they normally possess only a narrow spectrum of action against certain parasites. Agents which act against other parasites, for example Myxozoa or Microsporidia, are not at all available.

It has been found that the substituted 1,2,4-triazinediones of the general formula (I)

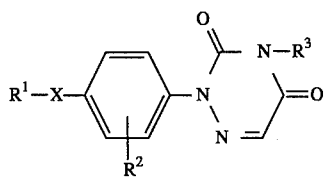

in which
$R^1$ represents optionally substituted aromatic radicals, or represents optionally substituted heteroaromatic radicals which are linked via carbon
X represents O, S, SO, $SO_2$ or

$X^2$ represents one or more identical or different radicals from the group comprising hydrogen, halogen, nitro, alkyl, alkoxy, halogenoalkyl, halogenoalkoxy
$R^3$ represents hydrogen, optionally substituted alkyl, alkenyl, alkinyl, aralkyl and their salts with bases can be used for controlling fish parasites, in particular parasitic Protozoa and Metazoa, for example Plathelminthes.

Some of the triazinediones have been disclosed in EP-OS (European Published Specification) 170,316, which corresponds to U.S. Pat. No. 4,631,278 or they form the subject-matter of an earlier application by the applicant, which has not yet been published.

Substituted 1,2,4-triazinediones of the general formula (I)

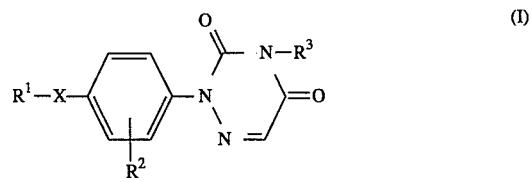

in which
$R^1$ represents optionally substituted heteroaromatic radicals which are bonded via carbon,
X represents O, S, SO, $SO_2$,
$R^2$ represents hydrogen one or more identical or different radicals from the group comprising hydrogen, halogen, nitro, alkyl, alkoxy, halogenoalkyl, halogenoalkoxy,
$R^3$ represents hydrogen, optionally substituted alkyl, alkenyl, alkinyl, aralkyl
can be prepared by a process in which
a) compounds of the formula (II)

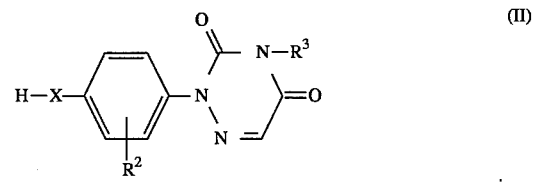

in which
X represents O or S,
$R^2 R^3$ have the abovementioned meaning are reacted with compounds of the formula (III)

in which
$R^1$ has the abovementioned meaning and
A represents the radicals halogen, O-$SO_2$-alkyl, -O-$SO_2$-halogenalkyl, -O-$SO_2$-aryl, -S-alkyl
or
b) for the preparation of compounds of the formula I in which $R^3$ does not represent hydrogen, compounds of the formula (Ia)

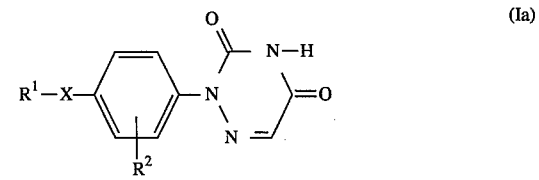

in which
$R^1$, $R^2$, X have the abovementioned meaning are reacted with compounds of the formula IV

in which
$R_3$ represents optionally substituted alkyl, alkenyl, alkinyl, aralkyl and
B represents halogen, -O-$SO_2$-alkyl, -O-$SO_2$-aryl, -O-$SO_2$-halogenoalkyl
or
c) for the preparation of compounds of the formula I in which X represents -SO- or -$SO_2$-, compounds of the formula I in which X represents S are reacted with an oxidant.

The compounds of the formula (II)

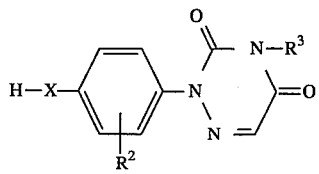
(II)

in which

X represents O or S,

R² represents one or more identical or different radicals on the group comprising halogen, nitro, alkyl, alkoxy, halogenoalkyl, halogenoalkoxy, and, in the event that X represents S, additionally represents hydrogen, R³ represents hydrogen, alkyl, alkenyl, alkinyl, aralkyl are novel and are obtained by decarboxylating compounds of the formula (V)

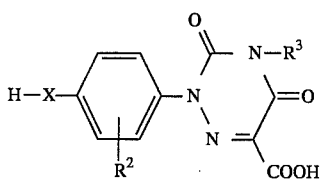
(V)

in which

X, R², R³ have the abovementioned meaning by heating.

The compounds of the formula (V)

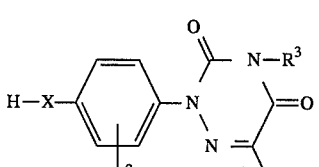
(V)

in which

X represents O or S,

R² represents one or more identical or different radicals from the group comprising halogen, nitro, alkyl, alkoxy, halogenoalkyl, halogenoalkoxy, and, in the event that X represents S, additionally represents hydrogen, R³ represents hydrogen, alkyl, alkenyl, alkinyl, aralkyl are novel and are obtained by heating compounds of the formula (VI)

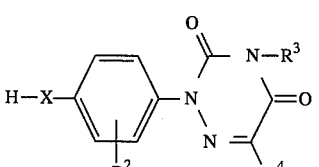
(VI)

in which

X, R², R³ have the meaning mentioned in (3),

R⁴ represents the radicals -CN,

R⁵ represents optionally substituted alkyl aryl in the presence of aqueous acids.

The compounds of the formula (VI)

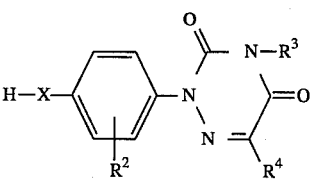
(VI)

in which

X, R², R³, R⁴ have the abovementioned meaning are novel and are obtained by heating compounds of the formula (VII)

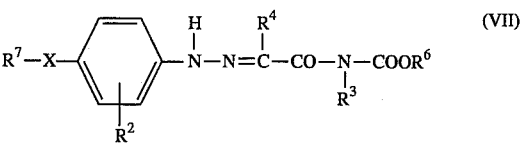
(VII)

in which

X, R², R³, R⁴ have the abovementioned meaning and

R⁶ represents alkyl or optionally substituted aryl,

R⁷ represents hydrogen or optionally substituted

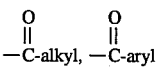

in the presence of bases.

The compounds of the formula (VII)

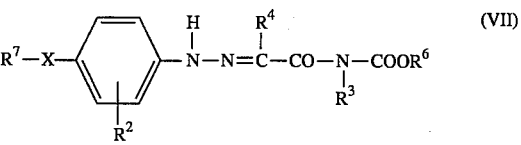
(VII)

in which

X, R², R³, R⁴, R⁶ and R⁷ have the abovementioned meaning and, in the event that R⁷ represents H or X represents S, R² can additionally represent hydrogen are novel and are obtained by initially diazotizing compounds of the formula (VIII)

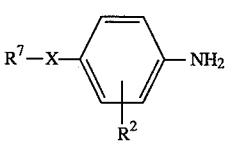
(VIII)

in which

X and R², R⁷ have the abovementioned meaning with alkali metal nitrite in the presence of aqueous mineral acids, and the reaction product is subsequently reacted with compounds of the formula (IX)

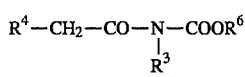  (IX)

in which

R³, R⁴ and R⁶ have the abovementioned meaning.

Preferably used compounds of the formula (I) are those in which

R¹ represents optionally halogen-, alkyl-, cyano-, nitro-, o-alkyl-, s-alkyl-, halogenoalkyl-substituted phenyl, thiazolyl, oxazolyl, benzothiazolyl or benzooxazolyl, X represents O, S or

$R^2$ represents halogen or $C_{1-6}$-alkyl, $R^3$ represents hydrogen or $C_1$–$C_4$-alkyl, in particular methyl.

Particularly preferably used compounds of the formula (I) are those in which

X represents O or

$R^1$ represents thiazolyl, benzothiazolyl, benzoxazolyl or phenyl, each of which is optionally substituted $C_{1-4}$-alkyl, in particular methyl, $C_{1-4}$-halogenoalkyl, in particular trifluoromethyl, halogen, in particular chlorine, bromine, fluorine, nitro, CN, $C_{1-4}$-alkoxy, in particular methoxy, $C_{1-4}$-halogenoalkoxy, in particular trifluoromethoxy, $C_{1-4}$-alkylthio, in particular methylthio, $C_{1-4}$-halogenoalkylthio, in particular trifluoromethylthio, $R^2$ represents one or more radicals from the group comprising hydrogen or halogen, in particular chlorine, bromine, $C_{1-4}$-alkyl, in particular methyl, $R^3$ represents hydrogen.

Very particularly preferably used compounds of the formula (I) are those in which X represents O, $R^1$ represents optionally chlorine- or methyl- or trifluoromethyl-substituted thiazolyl or benzothiazolyl, $R^2$ represents one or more radicals of the group comprising hydrogen, methyl or chlorine, $R^3$ represents hydrogen.

Other compounds of the formula (I) which are particularly preferably used are those in which X represent

$R^1$ represents phenyl which is optionally substituted by chlorine, methyl, trifluoromethyl, $R^2$ represents one or more identical or different radicals from the group comprising hydrogen, chlorine, methyl, $R^3$ represents hydrogen or methyl.

In particular, the following compounds may be mentioned:

2-Chloro-α-(4-chlorophenyl)-4-(4,5-dihydro-3,5-diozo-1,2,4-triazin-2(3H)-yl)-phenylacetonitrile and 2,6-Dichloro-α-(4-chlorophenyl)-4-(4,5-dihydro-3,5-dioxo-1,2,4-triazin-2(3H)-yl)-phenylacetonitrile.

Furthermore, the following individual compounds may be mentioned:

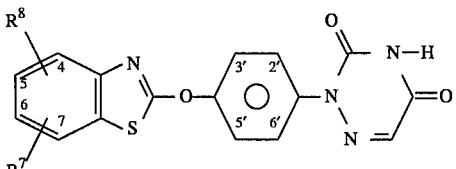

| R₂ | R⁷ | R⁸ |
|---|---|---|
| 3-CH₃ | 6-Cl | H |
| 3-CH₃ | 6-CF₃ | H |
| 3-CH₃ | 5-Cl | 6-Cl |
| 3,5-Cl | 6-Cl | H |
| 3,5-Cl | 6-CF₃ | H |
| 3,5-Cl | 5-Cl | 6-Cl |

Moreover, the following compounds may be mentioned:

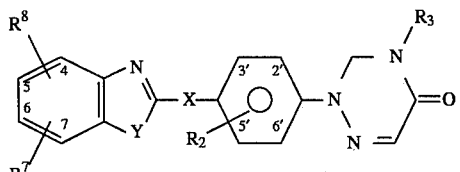

| Y | R₂ | X=0 R₃ | R₇ | R₈ |
|---|---|---|---|---|
| S | H | H | H | H |
| S | H | H | 6-Cl | H |
| S | H | H | 6-Br | H |
| S | H | H | 6-F | H |
| S | H | H | 6-CH₃ | H |
| S | H | H | 6-OCH₃ | H |
| S | H | H | 6-NO₂ | H |
| S | H | H | 6-CN | H |
| S | H | H | 6-CF₃ | H |
| S | H | H | 6-SCF₃ | H |
| S | H | H | 6-OCF₃ | H |
| S | H | H | 5-Cl | 6-Cl |
| S | 3'-CH₃ | H | H | H |
| S | 3'-CH₃ | H | 6-Br | H |
| S | 3'-CH₃ | H | 6-F | H |
| S | 3'-CH₃ | H | 6-CH₃ | H |
| S | 3-CH₃ | H | 6-OCH₃ | H |
| S | 3-CH₃ | H | 6-NO₂ | H |
| S | 3-CH₃ | H | 6-CN | H |
| S | 3-CH₃ | H | 6-SCF₃ | H |
| S | 3-Cl | H | H | H |
| S | 3-Cl | H | 6-Cl | H |
| S | 3-Cl | H | 6-Br | H |
| S | 3-Cl | H | 6-F | H |
| S | 3'-Cl | H | 6-CH₃ | H |
| S | 3'-Cl | H | 6-OCH₃ | H |
| S | 3'-Cl | H | 6-NO₂ | H |
| S | 3'-Cl | H | 6-CN | H |
| S | 3'-Cl | H | 6-CF₃ | H |
| S | 3'-Cl | H | 6-SCF₃ | H |
| S | 3'-Cl | H | 6-OCF₃ | H |
| S | 3'-Cl | H | 5-Cl | 6-Cl |
| S | 3',5'-Cl | H | H | H |
| S | 3',5'-Cl | H | 6-Br | H |
| S | 3',5'-Cl | H | 6-CH₃ | H |
| S | 3',5'-Cl | H | 6-OCH₃ | H |

-continued

| | | | | |
|---|---|---|---|---|
| S | 3',5'-Cl | H | 6-NO₂ | H |
| S | 3',5'-Cl | H | 6-CN | H |
| S | 3',5'-Cl | H | 6-SCF₃ | H |
| S | 3',5'-Cl | H | 6-OCF₃ | H |
| S | 3'-Cl, 5'-CH₃ | H | H | H |
| S | 3'-Cl, 5'-CH₃ | H | 6-Cl | H |
| S | 3'-Cl, 5'-CH₃ | H | 6-Br | H |
| S | 3'-Cl, 5'-CH₃ | H | 6-F | H |
| S | 3'-Cl, 5'-CH₃ | H | 6-OCH₃ | H |
| S | 3'-Cl, 5'-CH₃ | H | 6-CN | H |
| S | 3'-Cl, 5'-CH₃ | H | 6-CN | H |
| S | 3'-Cl, 5'-CH₃ | H | 6-CF₃ | H |
| S | 3'-Cl, 5'-CH₃ | H | 6-SCF₃ | H |
| S | 3'-Cl, 5'-CH₃ | H | 5-Cl | 6-Cl |
| S | 3'-CH₃, 5'-CH₃ | H | 6-Cl | H |
| S | 3'-CH₃, 5'-CH₃ | H | 5-Cl | 6-Cl |
| S | 3'-CH₃, 5-CH₃ | H | 5-Cl | H |
| S | 3'-Cl | H | 5-Cl | H |
| S | 3'-CH₃ | H | 5-Cl | H |
| S | 3'-Cl, 5'-CH₃ | H | 5-Cl | H |
| S | 3'-Cl, 5'-Cl | H | 5-Cl | H |
| S | 3'-Br | H | 6-Cl | H |
| S | 3'-Br, 5'-Br | H | 6-Cl | H |
| S | 3'-CF₃ | H | 6-Cl | H |
| S | 3'-CF₃, 5'-Cl | H | 6-Cl | H |
| O | 3'-Cl, 5'-Cl | H | 6-Cl | H |
| O | 3'-CH₃ | H | 6-Cl | H |
| S | 3'-Cl, 5'-Cl | CH₃ | 6-CL | H |
| S | 3'-CH₃ | —C₂H₅ | 5-Cl | 6-Cl |

| Y | X | R₂ | R₃ | R₇ | R₈ |
|---|---|---|---|---|---|
| S | S | H | H | 6-Cl | H |
| S | S | H | H | H | H |
| O | S | H | H | H | H |
| O | SO | H | H | H | H |
| O | SO₂ | H | H | H | H |
| O | S | 3,5-Cl₂ | H | 6-Cl | H |
| O | S | 3,5-Cl₂ | H | H | H |

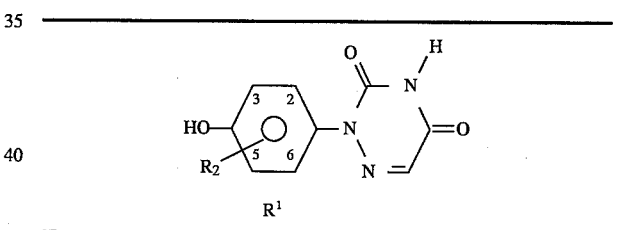

| Y | R₂ | R₃ | R₇ | R₈ |
|---|---|---|---|---|
| S | H | H | H | H |
| S | H | H | Cl | H |
| S | H | H | Cl | Cl |
| S | H | H | Cl | CF₃ |
| S | H | H | Cl | CH₃ |
| S | 3'-Cl | H | H | H |
| S | 3'-Cl | H | Cl | H |
| S | 3'-Cl | H | Cl | Cl |
| S | 3'-Cl | H | Cl | CF₃ |
| S | 3'-CH₃ | H | Cl | H |
| S | 3'-CH₃ | H | Cl | Cl |
| S | 3'-CH₃ | H | Cl | CF₃ |
| S | 3'-Cl, 5'-Cl | H | Cl | H |
| S | 3'-Cl, 5'-Cl | H | Cl | Cl |
| S | 3'-Cl, 5'-Cl | H | Cl | CF₃ |
| O | 3'-Cl, 5'-Cl | H | H | H |
| O | 3'-CH₃ | H | H | H |
| O | 3'-Cl, 5'-Cl | H | Cl | H |
| O | 3'-CH₃ | H | Cl | H |
| S | 3'-Cl, 5'-Cl | CH₃ | Cl | Cl |
| S | 3'-CH₃ | C₂H₅ | Cl | Cl |

If, in process 2, 2-(3,5-dichloro-4-hydroxyphenyl)- 1,2,4-triazine-3,5-(2H,4H)dione is employed as compound II and 2,6-dichlorobenzothiazole as compound of the formula III, the process may be described by the following equation.

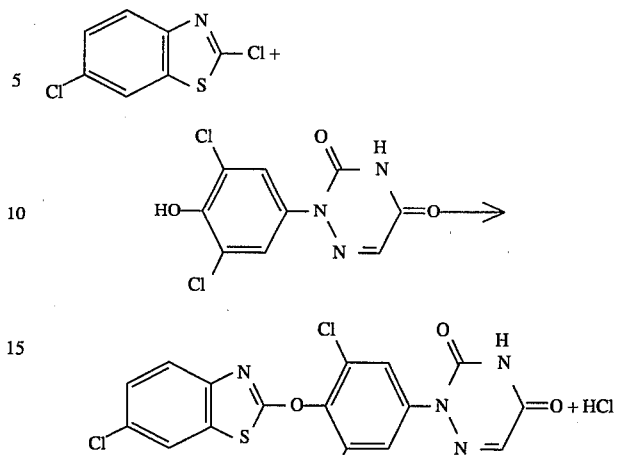

Compounds of the formula II in which
R² and R³ represent hydrogen are known (J. Slouka, Acta Unio Palacki Olomuk, Fac. Rerum. Nat. 1984 (Chem 23), 39–45; C.A. 102 203946c).

Compounds of the formula II in which R² represents radicals other than hydrogen are novel.

Compounds of the formula II which may preferably be mentioned are those in which R² and 3 have the meanings mentioned in the compounds of the formula I as being preferred.

The following novel compounds of the formula II may be mentioned individually.

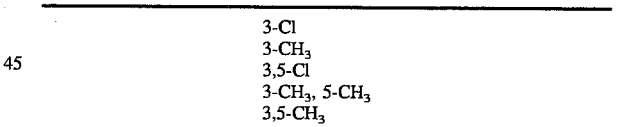

| R¹ |
|---|
| 3-Cl |
| 3-CH₃ |
| 3,5-Cl |
| 3-CH₃, 5-CH₃ |
| 3,5-CH₃ |

The substituted heterocycles of the formula III are known or may be prepared analogously to known processes (Beilstein Vol. 27; Katrizky and Rees, Comprehensive Het. Chem. Col. 6 1984).

They possess the preferred meanings indicated further above for the compounds of the formula I. The following compounds of the formula III may be mentioned individually.

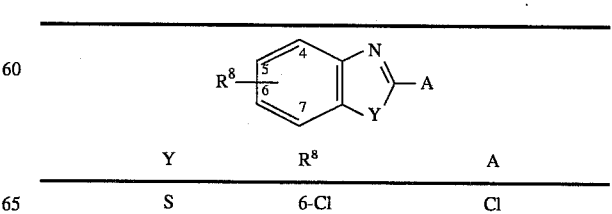

| Y | R⁸ | A |
|---|---|---|
| S | 6-Cl | Cl |

| -continued | | |
|---|---|---|
| S | 5,6-Cl | Cl |
| O | 6-Cl | Cl |
| O | 5,6-Cl | Cl |

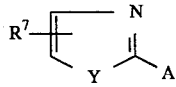

| Y | $R^7$ | A |
|---|---|---|
| S | 4-Cl | Cl |
| S | 4,5-Cl | Cl |
| O | 4-Cl | Cl |
| O | 4,5-Cl | Cl |

The reaction is preferably carried out using diluents.

Suitable diluents for this process are virtually all inert organic solvents. These preferably include aliphatic and aromatic, optionally halogenated hydrocarbons, benzine, ligroin, benzene, toluene, xylene, methylene chloride, ethylene chloride, chloroform, carbon tetrachloride, chlorobenzene and o-dichlorobenzene, ethers, such as diethyl ether and dibutyl ether, glycol dimethyl ether and diglycol dimethyl ether, tetrahydrofuran and dioxane, ketones, such as acetone, methyl ethyl ketone, methyl isopropyl ketone and methyl isobutyl ketone, esters, such as methyl acetate and ethyl acetate, nitriles, such as, for example, acetonitrile and propionitrile, amides, such as, for example, dimethylformamide, dimethylacetamide and N-methyl-pyrrolidone, and also dimethyl sulphoxide, tetramethylene sulphone and hexamethylphosphoric triamide.

The reaction is carried out in the presence of inorganic or organic acid acceptors.

Examples of acid acceptors which may be mentioned are:

Alkali metal hydroxides, such as, for example, sodium hydroxide and potassium hydroxide, alkaline earth metal hydroxides, such as, for example, calcium hydroxide, alkali metal carbonates and alkali metal alkoxides, such as sodium carbonate, potassium carbonate, sodium methoxide, potassium methoxide, sodium ethoxide and potassium ethoxide, furthermore aliphatic, aromatic or heterocyclic amines, for example triethylamine, pyridine, 1,5-diazabiccylo-[4,3,0]-non-5-ene (DBN), 1,8-diazabicyclo-[5,4,0]-undec- 7-ene (DBU) and 1,4-diazabicyclo-[2,2,2]-octane (DABCO).

The reaction is carried out at temperatures between 50° and 200° C., preferably between 80° and 160° C., at atmospheric pressure or increased pressure. The reaction is preferably carried out under atmospheric pressure.

The reaction is carried out by combining equimolar amounts of the compounds of the formula II and III in one of the diluents indicated, and heating the mixture. When the reaction is complete, the reaction mixture is acidified using dilute inorganic acid (for example hydrochloric acid), and the precipitate formed is filtered off, washed and dried.

If, in process 2b for the preparation of the compounds of the formula I in which $R^3$ does not represent hydrogen, 2-[4-2'-benzothiazolyloxyphenyl] 1,2,4-triazine-3,5-(2H,4H)-dione is employed as compound of the formula Ia and methyl iodide as compound of the formula IV, the protess may be described by the following outline.

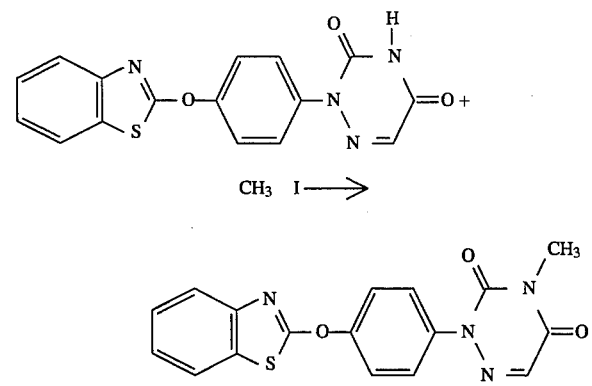

The compounds of the formula Ia are novel and are obtained as described in process 2a.

The compounds of the formula IV are known or may be prepared by known methods. Methyl iodide and ethyl bromide may be mentioned in particular.

The process is carried out by reacting a compound of the formula Ia with compounds of the formula IV in the presence of a base and of a diluent. Diluents which can be employed are all inert organic solvents which are also used for carrying out process Ia.

The process is carried out in the presence of bases. Preferred bases which may be mentioned are the alkali metal hydroxides, such as sodium hydroxide, alkali metal alkoxides, such as sodium methoxide or potassium butoxide, metal hydrides such as sodium hydride, or organic bases, such as 1,8-diazabicyclo[5,40]-undec-7-ene (DBU).

The process is carried out at atmospheric pressure and at temperatures between 20° and 140° C.

The reaction is carried out by combining equimolar amounts of the compound of the formula Ia and of the base, an equimolar amount of the compound of the formula IV is added to this mixture, and the mixture is heated to the reaction temperature.

If, in process 2c) for the preparation of the compounds of the formula I where X=SO or $SO_2$, 2-[4-[(2'-benzoxazolylthio)phenyl]- 1,2,4-triazine-3,5-(2H,4H)-dione is employed as compound of the formula I, the process may be described by the following outline.

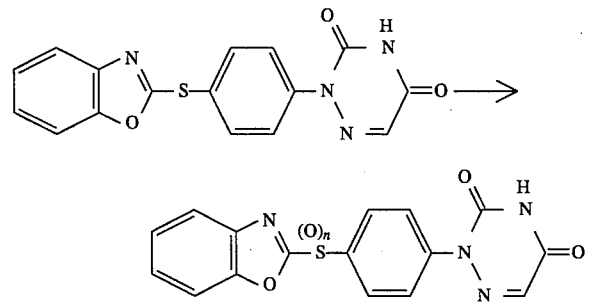

The process is carried out by treating a compound of the formula I where X=S with an oxidant in the presence of a diluent. Oxidants which are preferably used are: hydrogen peroxide and other inorganic peroxides, such as sodium peroxide, organic peroxo acids such as, for example, m-chloroperbenzoic acid, compounds of iodine and oxygen, such as, for example, sodium metaperiodate.

Diluents which can preferably be employed are: alcohols, such as, for example, methanol organic acids, such as, for example, acetic acid, and ketones such as acetone, halogenated hydrocarbons, such as dichloromethane, or acid anhydrides, such as acetic anhydride, can furthermore be used. The oxidation is carried out at temperatures between 0° C. and 120° C. The process is preferably carried out under atmospheric pressure.

The amount of oxidant can be varied within single molar and 10-fold molar. The reaction is carried out by stirring the compounds of the formula I where X=S together with one of the oxidants mentioned for several hours at the reaction temperature mentioned in one of the abovementioned diluents.

It was known that 1,2,4-triazinediones of the formula (I) in which

X represents

and

R¹ represents phenyl can be employed for controlling Coccidia of mammals and of birds. This action is also indicated for those compounds of the formula (I) which were hitherto unknown. Nothing was known about a possible use of the compounds of the formula (I) for the control of fish parasites.

Fish parasites include from the subkingdom of the Protozoa, species from the phylum of the Ciliata, for example *Ichthyophthirius multifiliis, Chilodonella cyprini, Trichodina spp., Glossatella spp., Epistylis spp.*, of the phylum of the Myxosporidia, for example *Myxosoma cerebralis, Myxidium spp., Myxobolus spp., Heneguya spp., Hoferellus spp.*, of the class of the Microsporidia, for example *Glugea spp., Thelohania spp., Pleistophora spp.*, from the phylum of the Plathelminthes: Trematodes; Monogenenea, for example *Dactylogyrus spp., Gyrodactylus spp., Pseudodactylogyrus spp., diplozoon spp.*, Cestodes, for example from the groups of the Caryphyllidea (for example *Caryophyllaeus laticeps*), Pseudophyllidea (for example *Diphyllobothrium spp.*), Tetraphyllidea (for example *Phyllobothrium spp.*) and Protocephalida (for example species of the genus Proteocephalus) and, from the phylum of the Arthropoda, various parasitic Gustacea, in particular from the subclasses of the Branchjura (fish lice) and Copepoda (copepods) and the orders of the Isopoda (isopods) and Amphipoda (waterfleas).

The fish include economically useful fish, cultured fish, aquarium fish and decorative fish of all ages which live in fresh water and sea water. The economically useful fish and cultured fish include, for example, carp, eel, trout, whitefish, salmon, bream, roach, rudd, dobule, sole, plaice, halibut, Japanese yellowtail (*Seriola quinqueradiata*), Japanese eel (*Anguilla japonica*), red sea bream (*Pagurus major*), sea bass (*Dicentrarchus labrax*), grey mullet (*Mugilus cephalus*), pompano, gilthread sea bream (*Sparus auratus*), *Tilapia spp.*, Chichlidae species such as, for example, Plagioscion, Channel catfish. The agents according to the invention are particularly suitable for treating fish fry, for example carps of body length 2–4 cm. The agents are also very suitable for eel fattening.

Treatment of t he fish is carried out either orally, for example via the feed or via short-term treatment, "medicinal bath", into which the fish are put and in which they are kept for a certain period (minutes up to several hours), for example when they are transferred from one rearing tank to the other.

However, transient or permanent treatment of the environment of the fish (for example of entire pond systems, aquariums, tanks or troughs) in which the fish are kept.

The active compound is supplied in the preparations which are designed to suit the applications.

Preparations for oral applications are powders, granules, solutions, emulsion concentrates or suspension concentrates, which are homogeneously mixed with the feed as feed additives.

The preparations are prepared in a manner known per se, by mixing the active compound with solid or liquid carriers, if appropriate with the addition of further active compounds and emulsifying or dispersing agents, solubilizers, colourants, antioxidants, preservatives.

The solid carriers include, for example, natural ground minerals, such as kaolins, clays, talc, chalk, diatomaceous earth, organic carriers, such as sugar, sucrose, lactose, fructose, cereal products, such as fine or coarse cereal meals, starch, animal meals, cellulose, powdered milk, inorganic carriers, such as common salt, carbonates, such as calcium carbonate, hydrogen carbonates, aluminum silica, silicates.

The liquid carriers and solubilizers include:

Water, alkanols, such as ethanol, isopropanol, glycols, such as ethylene glycol, propylene glycol, polyethylene glycols, polypropylene glycols and their copolymers, glycerol, aromatic alcohols, such as benzyl alcohol, phenylethanol, phenoxyethanol, esters, such as ethyl acetate, butyl acetate, benzyl benzoate, ethers, such as alkylene glycol alkyl ethers, such as dipropylene glycol monomethyl ether, diethylene glycol monobutyl ether, ketones, such as acetone, methyl ethyl ketone, aromatic and/or aliphatic hydrocarbons, vegetable or synthetic oils, DMF, DMSO, dimethylacetamide, N-methylpyrrolidone, 2-dimethyl-4-oxy-methylene- 1,3-dioxalone.

The dispersing and emulsifying agents include:

Non-ionogenic surfactants, such as polyoxyethylated castor oil, polyoxyethylated sorbitan monoleate, sorbitan monostearate, glycerol monostearate, polyoxyethylene stearate, alkyl phenol polyglycol ether, ampholytic surfactants, such as disodium lauryl β-iminodipropionate or lecithin, anion-active surfactants, such as sodium lauryl sulphate, fatty alcohol ether sulphates, monoethanol amine salts of mono/dialkyl polyglycol ether orthophosphates, cation-active surfactants, such as cetyltrimethylammonium chloride.

In the preparations, the concentration of active compound is approximately 1 ppm to 10 % by weight.

Preferred preparations for short-term treatment in the application as "medicinal bath", for example for the treatment when the fish are transferred or for the treatment of the habitat (pond treatment) of the fish are solutions of the active compound in one or more polar solvents which, upon dilution with water, show an alkaline reaction.

For the preparation of these solutions, the active compound is dissolved in a polar, water-soluble solvent which either shows an alkaline reaction or to which an alkaline, watersoluble sub stance is added. The latter is advantageously likewise dissolved in the solvent, but can also be suspended in the solvent to dissolve only upon contact with water. In this case, the water should have a pH of 7–10, but preferably a pH of 8–10, after the active compound solution has been added.

The active compound concentration can be in the range 0.5–50 %, but preferably in a range of 1–25 %.

Suitable solvents are all water-soluble solvents in which the active compound is soluble in a sufficient concentration and which are physiologically acceptable.

These solvents are ethyl alcohol, isopropyl alcohol, benzyl alcohol, glycerol, propylene glycol, polyethylene glycols, poly(oxyethylene)/poly(oxypropylene) polymers, basic alcohols, such as mono-, di- and triethanolamine, ketones, such as acetone or methyl ethyl ketone, esters, such as ethyl lactate, furthermore N-methylpyrrolidone, dimethylacetamide, dimethylformamide, furthermore dispersing and emulsifying agents, such as polyoxyethylated castor oil, polyethylene glycol sorbitan monooleate, polyethylene glycol stearate, or polyethylene glycol ether, polyethylene glycol alkylamines.

Bases which may be mentioned for adjusting the alkaline pH are organic bases such as basic amino acids, such as L- or D,L-arginine, L- or D,L-lysine, methylglucosamine, glucosamine, 2-amino-2-hydroxymethylpropane-(1,3)-diol, such as, furthermore, N,N,N',N'-tetrakis-(2-hydroxypropyl)ethylenediamine or polyether tetrol on the basis of ethylenediamine (M.W. 480–420), inorganic bases, such as ammonia or sodium carbonate, if appropriate with the addition of water.

The preparations can also contain 0.1 to 20 % by weight, preferably 0.1%–10 % by weight, of other formulation auxiliaries, such as antioxidants, surfactants, suspension stabilizers and thickeners, such as, for example, methylcellulose, alginates, polysaccharides, galactomannans and colloidal silica. It is also possible to add colorants, flavor and nutrient components for animal feeding. Acids which form a buffer system with the initially introduced base or which reduce the pH of the solution may also be mentioned in this context.

The active compound concentration for application depends on the type and duration of the treatment and on the age and condition of the treated fish. For example, for short-term treatment, it is 2–50 mg of active compound per liter of water, preferably 5–10 mg per liter, at a treatment period of 3–4 hours. For example, young carps are treated at a concentration of 5–10 mg/l and for a treatment period of approx. 1–4 hours.

Eels are treated with concentrations of approx. 5 mg/l for approx. 4 hours.

A corresponding lower concentration is chosen when the treatment period is longer or when permanent treatment is carried out.

For pond treatments, 0.1–5 mg of active compound can be used per liter of water.

Preparations for use as feed additive may have the following composition:

| | | |
|---|---|---|
| a) | Active compound of the formula I | 1–10 parts by wt. |
| | Soya-bean protein | 49–90 parts by wt. |
| b) | Active compound of the formula I | 0.5–10 parts by wt. |
| | Benzyl alcohol | 0.08–1.4 parts by wt. |
| | Hydroxypropylmethylcellulose | 0–3.5 parts by wt. |
| | Water | Remainder to 100 |

Preparations for use as "medicinal baths" and for pond treatment may have the following composition and may be prepared as follows:

| | | |
|---|---|---|
| c) | 2.5 g of active compound of Example 4 are dissolved in 100 ml of triethanolamine, with heating. | |
| d) | 2.5 g of active compound of Example 4, 12.5 g of lactic acid are dissolved in 100 ml of triethanolamine with heating and stirring. | |
| e) | 10.0 g of active compound of Example 4 are dissolved in 100 ml of monoethanolamine. | |
| f) | Active compound of formula I | 5.0 g |
| | Propylene glycol | 50.0 g |
| | Sodium carbonate | 5.0 g |
| | Water | to 100 ml |
| g) | Active compound of formula I | 5.0 g |
| | Monoethanolamine | 10 g |
| | N-methylpyrrolidone | to 100 ml |
| h) | Active compound of formula I | 2.5 g |
| | Sodium carbonate | 5.0 g |
| | Polyethylene glycol | 200 to 100 ml |

The active compound is dissolved in polyethylene glycol with heating, and sodium carbonate is suspended in the solution.

EXAMPLE A

In-vitro treatment of parasites

Parasites of the species mentioned were transferred to a glass dish containing 150 ml of water which had a temperature of 22° C. and to which the indicated concentration of active compound of Example 4 had been added. After the period of time indicated, the parasites were checked under an optical microscope. The following observations were made:

| Parasite | Conc./Time | Observation on the parasite |
|---|---|---|
| Ichthyophthirius multifiliis | 10 ppm/15 min | dead |
| Pseudodactylogyrus anguillae | 10 ppm/1–10 min | paralysis |
| Diplozoon homoion | 10 ppm/90 min | dead |

EXAMPLE B

In-vivo treatment of fish

Sticklebacks which were heavily infested with *Gyrodactylus arcuatus* were treated for 1 hours at 22° C. in 20 l of water to which 10 ppm of active compound of Example 4 had been added. After this, the fish were checked. They were free of parasites. The sediment contained dead or lethally damaged worms.

Examples of Active Compounds

Example 1

2-[4-[(4'Chloro)-2'-thiazolyloxy]phenyl]-3,5(2H, 4H)-dioxo-as-triazine

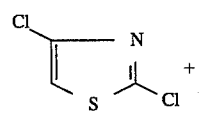

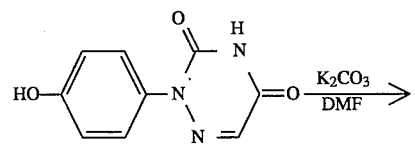

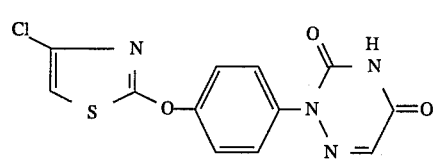

29 (0.01 mol) of hydroxyphenylazauracil, 1.5 g (0.01 mol) of dichlorothiazole and 1.4 g (0.01 mol) of potassium carbonate are stirred under reflux for 2 hours in 20 ml of dry DMF. The reaction mixture is cooled and acidified using HCl, and any product precipitated is filtered off with suction. After recrystallization of ethanol, 2.9 g (90% of theory) of thiazolyloxyarylazauracil are obtained.

The following are prepared analogously

Example 2

2-[-[4'-Chloro-5'-methyl)-2'-thiazolyloxy]phenyl]1,2,4-triazin-3,5(2H,4H)dione.

Example 3

2-(4-(2-Benzothiazolyloxy)-phenyl-1,2,4-triazine-3,5 (2H,4H)dione.

Example 4

2-[4[6'-Chloro)2'-benzothiazolyloxy]-3,5-dichlorophenyl]- 1,2,4-triazine-3,5(2H,4H)dione.

Example 4 a

2- [4-[6 '-Trifluoromethyl)2'-benzthiazolyloxy]-3,5-dichlorophenyl[1,2,4-triazine-3,5 (2H, 4H) dione

Example 4 b

2-[4-[6'-Trifluoromethoxy)2'-benzthiazolyloxy]-3,5-dichlorophenyl] 1,2,4-triazine-3,5 (2H, 4H) dione

Example 4 c

2-[4-[6'-Trifluoromethylthio)2'-benzthiazolyloxy]-3,5-dichlorophenyl-1,2,4-triazine-3,5 (2H, 4H) dione

Example 4 d

2-[4-[5', 6'-Dichloro)2'-benzthiazolyloxy]-3,5-dichlorophenyl] 1,2,4-triazine-3,5 (2H, 4H) dione

Example 5

2-[4-[4(4'-Chloro)-2'-thiazolyloxy]phenyl]-3-N-methyl-3,5-(2H,4H)-dioxo-1,2,4-triazine

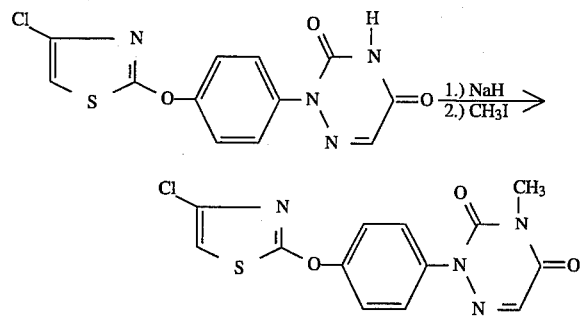

2 g (6 mmol) of thiazolyloxyarylazauracil are dissolved in 20 ml of absolute DMSO, and 0.14 g (6 mmol) of sodium hydride are added to the solution. The mixture is stirred at reflux temperature for 20 minutes, and 1.3 g (9 mmol) of methyliodide in 5 ml of DMSO are then added under argon. The mixture is warmed at 50° C. and maintained at this temperature for 3 h. Subsequently, the reaction mixture is concentrated in vacuo, and water is then added. After the solid precipitate has been filtered off with suction, 1.5 g (71% of theory) of the N-methyl compound are thus obtained.

Example 6a

2-[4-[6'-Chloro)2'-benzoxazolylsulphoxyl]-3,5-dichlorophenyl] 1,2,4-triazine-3,5(2H,4H)dione.

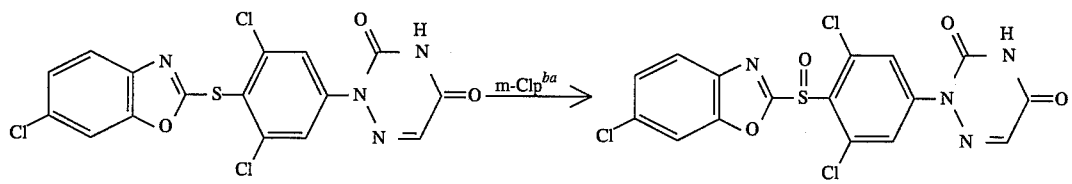

10 g (0,027 mol) of chlorobenzoxazolylthiophenylazauracil are dissolved in a mixture of 200 ml of methanol and 100 ml of dichloromethane. The mixture is cooled to 10° C., and 4.6 g of m-chloroperbenzoic acid (85 % strength) are added at this temperature. Stirring is continued at 10° C. for 10 h, the solvent is then stripped off in vacuo, and the residue is recrystallized from isopropanol. 8.5 g (82 % of theory) of sulphoxide are thus obtained.

Example 6b

2-[4-(2'-Benzoxazolylsulphoxyl)-3,5-dichlorophenyl)1,2,4-triazine- 3,5(2H,4H)dione.

Example 7

2-[4-(2'-Benzoxazolylsulphoxyl)-3,5-dichlorophenyl]1,2,4-triazine- 1,2,4,triazine-3,5(2H,4H)dione.

Example 8

2-[4-[(6'-Chloro)-2'-benzoxazolylsulphonyl]-3,5-dichlorophenyl] 1,2,4-triazine-3,5(2H,4H)dione.

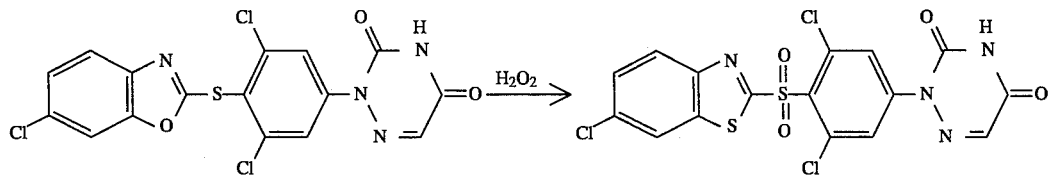

8.8 g (0.02 mol) of chlorobenzoxazolylthiophenylazauracil are dissolved in 100 ml of glacial acetic acid, and the solution is stirred under reflux with 40 ml of 30% strength hydrogen peroxide for 18 h. After the mixture has cooled down, water is added, and the precipitate formed is filtered off with suction. Recrystallization from isopropanol yields 6.9 g of sulphone (73% of theory).

Example 9

2-[4-(2'-Benzoxazolylsulphonyl)-3,5-dichlorophenyl]1,2,4-triazine- 3,5(2H,4H)dione.

Example 10

2-[4-(2'-Benzoxazolylsulphonyl)-phenyl]1,2,4-triazine-3,5(2H,4H)dione.

Example of the preparation of starting compounds of the formula II 2-(4-Hydroxyphenyl)-1,2,4-triazine-3,5(2,4H)dione

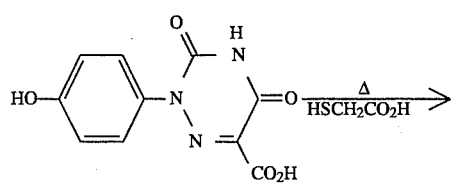

34 g (0.137 mol) of carboxylic acid are heated in 34 ml of mercaptoacetic acid at 170° C. After 1.5 h, the mixture is allowed to cool, water is added, the mixture is filtered off and 24 g (82% of theory) of decarboxylated product are then obtained.

Example of the preparation of the starting compounds of the formula V 2-(4-Hydroxyphenyl)-3,5(2H,4H)dioxo-1,2,4-triazine-6-carboxylic acid

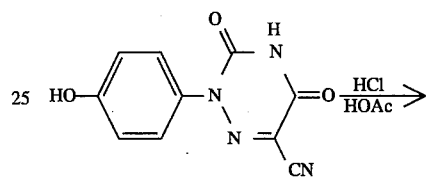

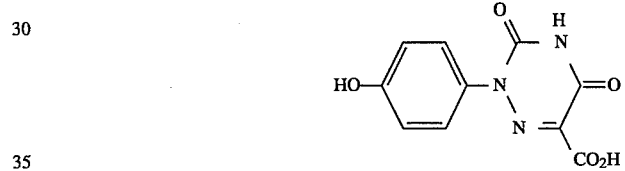

30.1 g (0.13 mol) of cyanoazauracil are stirred under reflux in 1000 ml of HCL/blacial acetic acid (1:1) for 14 h. The mixture is allowed to cool and then concentrated, water is added to the residue and the precipitated product is filtered off with suction 19 g (59% of theory).

Example of the preparation of starting compounds of the formula VI 2-(4-Hydroxyphenyl)-3,5-(2H,4H)dioxo-6-cyano-1,2,4-triazine

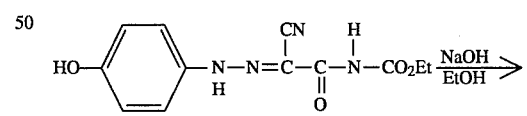

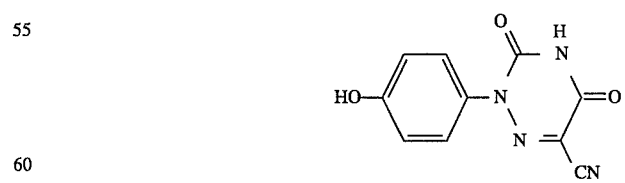

43.8 g (0.158 mol) of hydrazonocyanurethane, 8.5 g (0.213 mol) of NaOH are refluxed for 2 h in 400 ml of abs. ethanol. The mixture is subsequently cooled, acidified using hydrochloric acid and concentrated in vacuo. The batch is stirred with water, and the precipitate formed is filtered off with suction. After drying, 30.1 g (85 of theory) of cyanoazauracil are thus obtained.

Example of the preparation of the starting compounds of the formula VII

Ethyl-N-[[[cyano(4-hydroxyphenyl)-hydrazinylidene]-methyl]-carbonyl]-carbamate

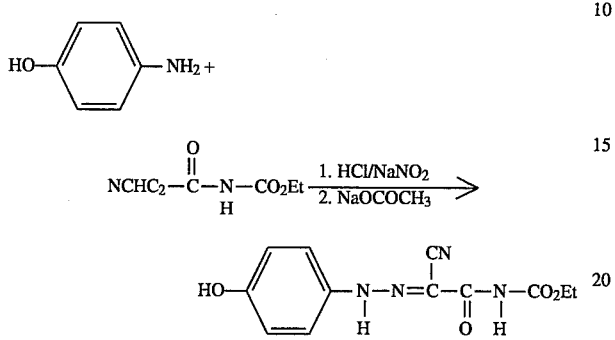

10 g (0.091 mol) of 4-hydroxyaniline are dissolved in 19.7 ml of conc. HCl and 200 ml of glacial acetic acid, and a solution of 6.4 g (0.092 mol) of sodium nitrite in 30 ml of water are added dropwise to the solution at 0°–5° C. Stirring is continued until a clear solution has formed, a mixture of 14.3 g (0.092 mol) of cyanoacetylurethane and 21 g (0.25 mol) of sodium acetate is then added, and stirring is continued at 10° C. for 3 h. The reaction mixture is concentrated in vacuo, water is added, and the sol id is filtered off with suction. In this way, 19 g (75%) of product are obtained as a finely-crystalline, yellow powder.

What is claimed is:

1. A method for controlling fish parasites comprising administering to fish having such parasites or to a habitat of fish having such parasite at least one triazinedione of the formula

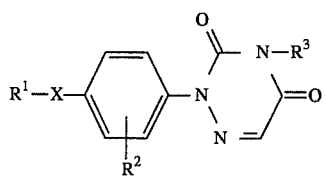

in which

X represents O, S, SO or SO$_2$;

R$^1$ represents phenyl, thiazolyl, oxazolyl, benzothiazolyl or benzoxazolyl each of which is optionally substituted by C$_{1-4}$-halogenoalkyl, halogen, nitro, CN, C$_{1-4}$-alkoxy, C$_{1-4}$-halogenoalkoxy, C$_{1-4}$-alkylthio or C$_{1-4}$-halogenoalkylthio;

R$^2$ represents hydrogen or one or more halogen or C$_{1-6}$-alkyl radicals; and R$^3$ represents hydrogen or C$_{1-4}$-alkyl in an amount effective to control fish parasite.

2. A method according to claim 1, wherein X represents O or S.

3. A method according to claim 1, wherein X represents O.

4. A method according to claim 1 wherein R$^1$ represents phenyl which is optionally substituted by chlorine; and R$^2$ represents one or more chlorine atoms.

5. A method for controlling fish parasites comprising administering to fish having such parasites or to a habitat of fish having such parasites an effective amount therefor of at least one triazinedione of the formula

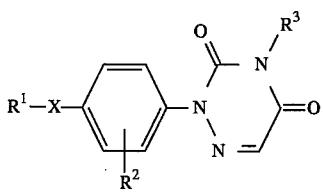

in which

X represents O,

R$^1$ represents optionally chlorine-, methyl-, trifluoromethyl-, trifluoromethoxy- or trifluoromethylthio,substituted thiazolyl or benzothiazolyl, R$^2$ represents hydrogen or one or more halogen or C$_{1-6}$-alkyl radicals; and R$^3$ represents hydrogen.

6. A method according to claim 5, in which the at least one triazinedione is selected from the group consisting of 2-[4-[6'-Trifluoromethyl] 2'-benzthiozolyloxy]-3,5dichlorophenyl] 1,2,4-triazine-3,5(2H,4H) dione, 2-[4-[6'-trifluoromethoxy)2'-benzthiazolyloxy]-3, 5dichlorophenyl] 1,2,4-triazine-3,5(2H,4H) dione, 2-[4-[6'-Trifluoromethylthio)2'-benzthiazolyloxy]- 3,5-dicbiorophenyl]1,2,4-triazine-3,5(2H,4H) dione and 2-[4-[5', 6'-dichloro) 2'-benzthiazolyloxy]- 3,5-dichlorophenyl]1,2,4-triazine-3,5 (2H, 4H) dione.

7. A method which comprises treating insects or productive, breeding aquarium or ornamental fishes infested with parasite protozoa or metazoa by administering an effective amount of a compound of the formula (I)

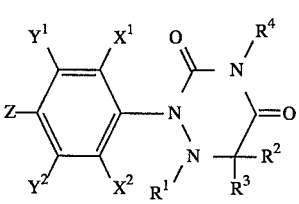

in which R$^1$ represents together with R$^2$ a chemical bond, R$^2$ represents together with R$^1$ a chemical bond, R$^3$ represents hydrogen, C$_1$–C$_{12}$ alkyl, R$^4$ represents hydrogen, straight-chain or branched C$_1$–C$_{12}$ alkyl, X$^1$, X$^2$, Y$^1$, Y$^2$ represent hydrogen, halogen, C$_1$–C$_6$ alkyl, Z represents phenoxy, phenylthio, phenylsulfinyl, phenylsulfonyl each of which is unsubstituted or substituted by hydrogen, trifluoromethyl, C$_1$–C$_6$ alkoxy, C$_1$–C$_6$ alkylthio.

8. A method which comprises treating insects or productive, breeding aquarium or ornamental fishes infested with parasite protozoa or metazoa by administering an effective amount of a compound of the formula (I)

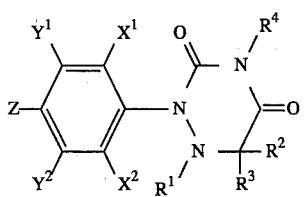

in which $R^1$ represents together with $R^2$ a chemical bond; $R^2$ represents together with $R^1$ a chemical bond; $R^3$ represents hydrogen; $R^4$ represents hydrogen, straight-chain or branched $C_1$–$C_{12}$ alkyl or benzyl; $X^1$, $X^2$, $Y^1$, $Y^2$ represent hydrogen, halogen, $C_1$–$C_6$ alkyl, $C_1$–$C_6$ alkoxy or trifluoromethyl; Z represents phenoxy, phenylthio, phenylsulfinyl, phenylsulfonyl or 1-cyano-1-phenylmethyl, each of which is unsubstituted or substituted on the phenyl ring by a substituent selected from the group consisting of halogen, trifluoromethyl, nitro, cyano, $C_1$–$C_6$ alkyl, $C_1$–$C_6$ alkoxy and $C_1$–$C_6$ alkylthio.

* * * * *

UNITED STATES PATENT AND TRADEMARK OFFICE
CERTIFICATE OF CORRECTION

PATENT NO. : 5,464,837
DATED : November 7, 1995
INVENTOR(S) : Mehlhorn, et al.

It is certified that error appears in the above-indentified patent and that said Letters Patent is hereby corrected as shown below:

Col. 19, line 39     Delete " parasite " and substitute
                         parasites Col. 20, line 37     Delete " dicbiorophenyl " and substitute
                         --dichlorophenyl--

Signed and Sealed this

Twenty-sixth Day of March, 1996

Attest:

BRUCE LEHMAN

Attesting Officer     Commissioner of Patents and Trademarks